US00PP27837P2

(12) United States Plant Patent
Hansen

(10) Patent No.: US PP27,837 P2
(45) Date of Patent: Apr. 4, 2017

(54) ***HIBISCUS* PLANT NAMED 'MOCHA MOON'**

(50) Latin Name: ***Hibiscus* hybrid (L.)**
Varietal Denomination: Mocha Moon

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 78 days.

(21) Appl. No.: 14/756,232

(22) Filed: Aug. 19, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Anne Grunberg

(57) ABSTRACT

A new and distinct cultivar of hardy herbaceous perennial *Hibiscus* hybrid plant named 'Mocha Moon' comprising an upright branched stems, numerous, outward-facing, near light pink to white flowers over a prolonged season having a lustrous scarlet-red eye and short radiating veins. The foliage is deep bronze-green, primarily tri-lobed.

1 Drawing Sheet

Botanical classification: *Hibiscus* hybrid (L.).
Variety denomination: 'Mocha Moon'.

BACKGROUND AND ORIGIN OF THE PLANT

The present invention relates to the new and distinct hardy, herbaceous, *hibiscus* plant, *Hibiscus* 'Mocha Moon' hybridized by the inventor on Jul. 27, 2011 at a nursery in Zeeland, Mich. The new plant, originally labeled # 11-117-105, is a single seedling selection from a cross between *Hibiscus* 'Crown Jewels' U.S. Plant Pat. No. 11,857 (female pod parent) times *Hibiscus* 'Midnight Marvel' U.S. Plant Pat. No. 24,079 (male pollen parent). The seed was harvested on Nov. 11, 2011 the specific seedling passed the initial trial in the summer of 2012. Both parents have a complex mixture of species in them, most likely including the species: moscheutos and coccineus. *Hibiscus* 'Mocha Moon' was first asexually propagated in 2013 by both stem tip cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Mocha Moon' differs from its parents as well as all other hardy herbaceous *hibiscus* known to the applicant in many traits. The foliage color of 'Mocha Moon' is greyed-purple with generally tri-lobed foliage. The most similar *hibiscus* in flower color known to the applicant is 'Crown Jewels', the female parent, but the flowers of the new plant are larger and the habit more compact and less spreading. The new plant is similar to 'Midnight Marvel', the male parent, in foliage coloration but the flower of 'Midnight Marvel' is a scarlet red with no white to light pink and the flower of 'Mocha Moon' is also flatter and less cupped. Compared to 'Starry Starry Night' (co-pending application having U.S. Plant Ser. No. 14/756,230) the new plant is later flowering and the petals do not have the long scarlet veins and pinwheel color pattern. Compared to 'Cherry Cheesecake' (U.S. Plant Pat. No. 26,089) the petals of the new plant are flatter and not as folded along the veins, and the petal background is nearer white without the magenta veins that extend to the apex. The foliage of the new plant also differs from 'Cherry Cheesecake' in that it is more tri-lobed and deep bronze-green. Other similar *hibiscus* including: 'Perfect Storm' co-pending U.S. Plant patent application Ser. No. 14/757,106, 'Summer Storm' U.S. Plant Pat. No. 20,443, 'Tie Dye' U.S. Plant Pat. No. 24,078. Table 1 below shows further comparisons to similar cultivars.

TABLE 1

| CULTIVAR | Foliage color | Leaf shape | Flower color | Habit | Size (H × W) |
|---|---|---|---|---|---|
| 'Cherry Cheesecake' | dark green with purple overtones | ovate to tri-lobed | white, magenta tips, veins, and eye | upright mound | 145 cm × 140 cm |
| 'Crowned Jewels' | medium green | ovate | pink rose pinwheel, rose eye | upright mound | 120 cm × 110 cm |
| 'Midnight Marvel' | dark burgundy | palmate | scarlet red | compact mound | 120 cm × 120 cm |
| 'Mocha Moon' | deep bronze-green | tri-lobed | white with scarlet eye | broad mound | 120 cm × 170 cm |
| 'Starry Starry Night' | dark purplish | tri-lobed | white and pink pinwheel, scarlet eye | mound | 120 cm × 120 cm |
| 'Summer Storm' | dark burgundy | palmate | pink, rose veining, magenta eye | upright mound | 160 cm × 160 cm |
| 'Tie Dye' | medium green | tri-lobed | White and cherry red bull's eye pattern | upright mound | 150 cm × 150 cm |

*Hibiscus* 'Mocha Moon' is a unique hardy herbaceous *hibiscus* with the following combined traits:

1. Hardy perennial with dense branching producing a low mound.
2. Many flowers over a prolonged season having light pink to near white background and a scarlet-red lustrous eye with short radiating veins.
3. Deep bronze-green, heavily-dissected primarily tri-lobed foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
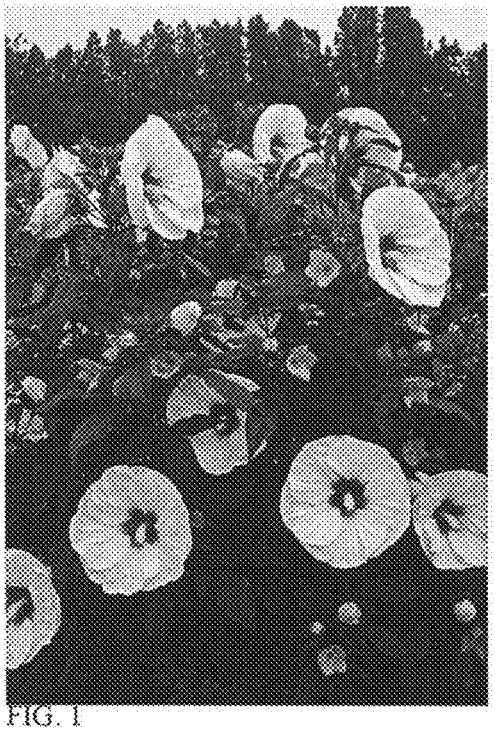
FIG. 1 shows a three-year old plant in the landscape.
Figure 2:
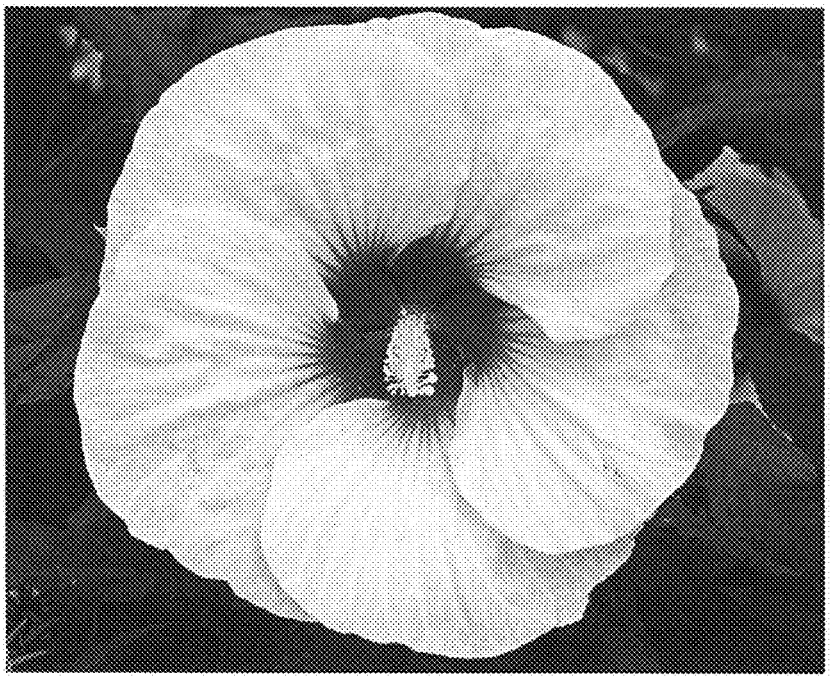
FIG. 2 shows a close-up of the flowers with white to light pink petals and scarlet radiating eye.

The following descriptions and color references are based on the 2001 edition of The Royal Horticultural Society Colour Chart except where common dictionary terms are used. The new plant, *Hibiscus* 'Mocha Moon', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full- sun trials of a nursery in Zeeland, Mich. with supplemental fertilizer and water as needed. The plants are natural habit and were not treated with plant growth regulators, nor were they pinched at any time in the growth year.

Parentage: *Hibiscus* 'Crown Jewels' U.S. Plant Pat. No. 11,857 (female seed parent) times *Hibiscus* 'Midnight Marvel' U.S. Plant Pat. No. 24,079 (male pollen parent).

Propagation:

*Method.*—Stem cuttings and sterile plant tissue culture division.

*Time to initiate roots from tissue culture.*—About two weeks.

*Rooting habit.*—Normal, branching, developing thick to about 2.5 cm diameter, fleshy; root color creamy yellow between RHS 161D and lighter than RHS 159D depending on soil type.

*Crop time.*—Under normal summer growing conditions 12 to 16 weeks to flower in a four-liter container from cutting. Plant vigor is very good.

Plant description:

*Plant shape and habit.*—Hardy herbaceous perennial with 24 to 33 thick upright and heavily branched main stems producing a upright spreading mound about 95.0 cm tall and 150.0 cm wide, widest about 50 cm above soil line; 7 to 14 primary branches per main stem protruding at about 45° to 30° angle from horizontal, lateral branches on the middle half of the primary stems; lateral branch size: between 4.0 cm and 16 cm long (shorter at the upper nodes) and average 4.0 mm diameter at the base of branch; flowering on the upper ⅓ of the plant beginning at axillary nodes while still developing at the apex;

*Stem.*—Rounded, glabrous, glaucous; average about 90.0 cm tall and 3.5 cm diameter at base.

*Stem color.*—Between RHS N186B and RHS N187B.

*Internode.*—About 18 nodes per stem below flower and about 32 total, average internode length about 4.5 cm of unpinched plant, varied between 2.0 to 6.0 cm widest in middle portion of stem.

Foliage description: Alternate; dentate; glabrous; mostly deeply cleft tri-lobed, occasional five- lobed; with side lobes at about 80 degree angle from center lobe; adaxial texture lustrous in young expanding leaves and matte in proximal leaves; abaxial texture matte; leaf blade size to about 22.0 cm long and 20.0 cm wide, average 16.5 cm long and 15.0 cm wide, larger proximally and becoming smaller in distal portion of stem.

*Foliage color.*—Adaxial between RHS N186B and RHS N186C where exposed to high sunlight and nearest RHS 143B where protected from strong sunlight; abaxial mostly between RHS 146B and RHS 146C with some tinting of between RHS 187A and RHS 187B.

*Veins.*—Palmate; adaxial main vein nearest RHS 60A, secondary veins nearest RHS 187C; primary and secondary abaxial veins between RHS 184A and RHS 185B.

*Petioles.*—Average size 7.0 cm long and 5.0 mm wide; mostly cylindrical with slight flattening of adaxial basal 3.0 cm; glaucous, glabrous.

*Petiole color.*—Adaxial between RHS 184A and RHS 184B; abaxial blended between RHS 178B and RHS 184B in more light, where protected from light nearest RHS 146D.

Flower description:

*Buds.*—One day prior to opening about 6.0 cm long and 5.0 cm in diameter, rounded apex and bluntly rounded base, unopened petals wrinkled at veins; prior to showing petals buds are about 3.4 cm long and 2.5 cm in diameter, ovoid with acute apex, carinate at the sepal fusion seams.

*Bud color.*—Exposed petal nearest RHS 11D toward apex with vein tinting of between RHS 60C and RHS 60B, toward base of exposed petal lighter than RHS 11D; prior to showing petals color between RHS 143C and RHS 144B with veining nearest RHS 143C, sepal carina having very light tinting nearest RHS N186C.

*Epicalyx.*—Entire, smooth, puberulent both surfaces, linear with sharply acute apex and attenuate base, curved around sepals; typically 10 to 12 per flower; about 2.5 cm long tapering to base of about 3.0 mm wide.

*Epicalyx color.*—Adaxial and abaxial between RHS 141C and RHS 143A with slight tinting of nearest RHS 178C in high sunlight exposure.

*Sepals.*—Five, proximal half connate forming campanulate star-shaped calyx; acute apex; margin entire, edentate; puberulent abaxial glabrous adaxial; individually about 4.2 cm long and about 2.5 cm wide at fusion point; together about 7.0 cm across and about 2.0 cm deep.

*Sepal color.*—Abaxial between RHS 143C and RHS 144B, adaxial color between RHS 144B and RHS 143B.

*Flowers.*—Solitary, about 40 to 45 per main stem without pinching; primarily outwardly facing; average 18.5 cm across and 5.5 cm deep from outside face to center of petals, larger in early part of flowering season; persist for a one to two days; effective for at least 9 weeks beginning mid-August and lasting into October; no detectable fragrance.

*Petals.*—Five; glabrous, slightly lustrous in center and dull both front and back toward middle and perimeter, adnate to the androecium to form a column, imbricate to about 90% overlapping at widest part (petals about 45% overlapping the next petal to either side), palmately veined, primary and secondary veins impressed on front and ribbed on back; shape: rounded; margins: entire, edentate; apex: rounded; base: short claw-like; surfaces: adaxial and abaxial glabrous; size: average about 8.5 cm long and about 11.0 cm wide at widest portion (largest in earlier part of flowering season); center dark eye about 5.0 cm diameter; veins extending from dark eye about 2.3 cm.

*Petal color*.—Adaxial background near white, lighter than RHS 155D, center eye between RHS 60A and RHS 60B with veins and slight blushing on petal side covered by next petal counter-clockwise nearest RHS 60C; abaxial color background whiter than RHS 155D, with blushing lighter than RHS N57D toward apical one third; abaxial vein color whiter than RHS 155D.

*Gynoecium*.—Style: enclosed in column about 5.5 cm long and 1.5 cm wide at base; column color nearest RHS 11D; style protruding from column and split in distal 7.0 mm portion into typically five branches, branch diameter 2.0 mm; branch color nearest RHS 155D. Stigma: typically five; globose, puberulose, about 3.0 mm in diameter; color nearest RHS 11D. Ovary: superior, about 6.5 mm across at base and 6.0 mm tall; acute apex; color between RHS 145B and RHS 145C.

*Androecium*.—Filaments: numerous, about 140; less than 1.0 mm in diameter and about 5.0 mm long; attached along nearly the entire length of column; color nearest RHS 155D. Anthers: reniform; about 2 mm long and 1 mm wide; nearest RHS 161C. Pollen: numerous, globose, less than 0.1mm long; color between RHS 156C and RHS 161C.

*Pedicel*.—Rounded in cross section, finely puberulent; length from base of sepal to abscission point average 1.5 cm long and 4.0 mm wide, longer on early flowers decreasing in later flowers; color between RHS 146C and RHS 146D.

*Peduncle*.—Rounded, puberulent, average about 4.0 cm long from abscission point to stem and 2.5 mm wide, slightly longer on earlier flowers.

*Peduncle color*.—Between RHS 61A and RHS 60B.

*Fruit*.—Few, loculicidal capsule; glabrous; globose, occasionally with abruptly acute apex; color between RHS N199B and RHS N199C when mature.

*Seed*.—Minutely floccose, typically globose; about 3.0 mm in diameter; color between RHS 200A and RHS N199B.

Resistance: The plant grows best with plenty of moisture, but is able to tolerate some drought once established. Other pest and disease resistance beyond that of other hardy perennial *hibiscus* cultivars has not been observed. Hardiness at least from USDA zone 4 through 9.

I claim:

1. A new cultivar of hardy herbaceous perennial *Hibiscus* hybrid plant named 'Mocha Moon' as herein illustrated and described, suitable for potted plant culture, landscaping as a specimen or en masse, and especially suited for patios and confined spaces because of the compact habit.

* * * * *